United States Patent [19]
Razdolsky et al.

[11] Patent Number: 5,735,688
[45] Date of Patent: Apr. 7, 1998

[54] ATTACHMENTS FOR A MANDIBULAR DISTRACTION DEVICE FOR USE IN MANDIBULAR DISTRACTION OSTEOGENESIS

[76] Inventors: Yan Razdolsky, 600 Lake Cook Rd., Suite 150, Buffalo Grove, Ill. 60089; Patrick John Driscoll, 203 E. Olive, Prospect Heights, Ill. 60070

[21] Appl. No.: 606,033

[22] Filed: Feb. 22, 1996

[51] Int. Cl.$^6$ ............................ A61C 3/00; A61C 13/22
[52] U.S. Cl. ........................................... 433/7; 433/181
[58] Field of Search ........................... 433/7, 8, 13, 14, 433/181, 182

[56] References Cited

U.S. PATENT DOCUMENTS

| | | | |
|---|---|---|---|
| 1,304,721 | 5/1919 | Young | 433/13 |
| 1,369,665 | 2/1921 | Johnson | 433/14 |
| 1,520,809 | 12/1924 | Cohen | 433/181 |
| 1,705,504 | 3/1929 | Sorensen | 433/181 |
| 4,482,318 | 11/1984 | Förster. | |
| 4,579,528 | 4/1986 | Staubli | 433/181 |
| 4,713,000 | 12/1987 | Rosenberg. | |
| 5,364,396 | 11/1994 | Robinson et al.. | |

FOREIGN PATENT DOCUMENTS

| | | |
|---|---|---|
| 2 267 740 | 4/1975 | France. |
| 24 40 856 | 8/1974 | Germany. |

*Primary Examiner*—Nicholas D. Lucchesi
*Attorney, Agent, or Firm*—Wenderoth, Lind & Ponack

[57] ABSTRACT

Attachment are used with a mandibular distraction device for use in distracting the mandible subsequent to corticotomy thereof. First and second sets of crowns of the device are adapted to be attached to the bicuspid and molar teeth of respective opposite lateral sides of the mandible. A first pair of expander assemblies are removably or fixedly attachable to the opposite sides of the first set of crowns, and a second pair of expander assemblies are removably or fixedly attachable to the opposite sides of the second set of crowns. Each pair of expander assemblies includes one expandable device and one sliding tube assembly. The attachments include receptor attachments that are provided to be attached to the bicuspid crowns and the molar crowns, and corresponding connector attachments that are provided to be attached to the screw devices and sliding tube assemblies for connection thereof to the crowns.

10 Claims, 9 Drawing Sheets

ATTACHMENTS FOR A MANDIBULAR DISTRACTION DEVICE FOR USE IN MANDIBULAR DISTRACTION OSTEOGENESIS

BACKGROUND OF THE INVENTION

The present invention relates generally to the correction of deficiencies in mandibular growth. More specifically, the present invention relates to attachments for a device for mandibular distraction osteogenesis the (lengthening of the lower jaw by stretching) for correcting deficiencies in mandibular length.

Deficiencies in mandibular growth which lead to characteristic protrusions of the maxillary teeth and deficiencies of the chin are quite common in American and Northern European populations. Data from recent large scale U.S. Public Health Service surveys of the occlusion of children and youth ages 6 through 10 indicate that about 20 percent of the U.S. population has mandibular deficiency, and about 5 percent of the total U.S. population has skeletal mandibular deficiency (deficiency in the growth of the lower jaw) so severe that the only way to correct such deficiency is to perform a total mandibular (lower jaw) resection (osteotomy) and to advance the lower jaw to a more favorable forward position.

Figure 1:
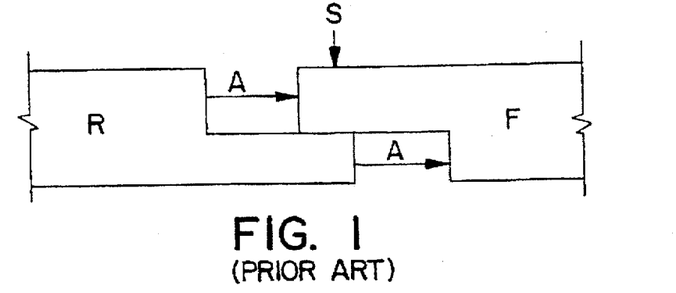
FIG. 1 is a schematic drawing illustrating sagittal split osteotomy surgery.

A total mandibular osteotomy, or a sagittal split osteotomy, is a major surgical procedure that can have many complications. In this procedure, as illustrated in FIG. 1, a human mandible is split at opposite points on the mandible. The forward part of the mandible is then brought apart from the rearward part and stabilized with either: (1) screws at point S as labeled in the figure (the forward part F is indicated in FIG. 1 by the arrows A as having been moved; this procedure is used less commonly now than in previous years due to the inherent difficulty in positioning of three loose parts of the mandible correctly during the surgery) or (2) splinting of the broken lower jaw to a prefabricated interocclusal splint which is secured to the upper jaw and allowing it to heal for approximately 2 months (during which the patient cannot open his/her mouth, cannot communicate or function and is fed through a straw).

This procedure cuts the bone marrow, and thus could be detrimental to the inner nerves and blood vessels of the mandible.

In addition, a total mandibular osteotomy can involve the complications of bleeding, obstruction of the airway, possible infection, neurological problems such as possible paralysis of the inferior alveolar nerve and loss of sensation to the lip, failure of intermaxillary fixation (stabilization of the mandible after surgery), relapse-movement of the lower jaw in the direction from which it was advanced, and possible displacement of the temporo-mandibular jaw joints during the surgery.

Needless to say, such surgery requires a hospital stay, is very expensive and many patients are reluctant to agree to this. Further, total treatment time is on the order of 30 months.

The other 15 percent of mandibular deficiencies are less severe, and if they are caught early, during the pubertal growth stage, are amenable to conventional orthodontics (braces) or a combination of orthodontics and functional appliance treatment. However, functional appliances are of most benefit to a patient when the patient is undergoing body and jaw growth, and cannot benefit adult (non-growing) patients.

One other prior art surgical technique bears mention. A process of lengthening human long bones (limbs, arms, etc.) by distraction osteogenesis has been utilized for the past 40 years. This process was designed by a Russian surgeon, Dr. Gavriel A. Ilizarov. The principles of the method of Dr. Ilizarov are presented in an article based on a speech delivered by Dr. Ilizarov on Oct. 30, 1987 at the annual Scientific Program of the Alumni Association and material presented by Dr. Ilizarov at a three day international conference on the Ilizarov techniques for the management of difficult skeletal problems. His technique is being widely used by orthopedic surgeons throughout the United States and the world.

SUMMARY OF THE INVENTION

The object of the present invention is to provide attachments for an appliance or device for distraction osteogenesis that is applicable to the five percent of severe cases requiring surgery as well as to the less severe 15 percent of cases if those cases have missed their opportunity for orthodontic/functional correction during their pubertal growth years. Distraction osteogenesis is, by definition, the process of generating new bone by stretching. Thus the present invention provides attachments for a device for generating new mandibular bone by stretching the mandible, while orthodontically lengthening the mandible and minimizing the extent of the conjunctive lower jaw surgery.

The objects of the present invention are met by the use of attachments for a device used in a method of mandibular distraction osteogenesis. This method involves performing corticotomy surgery, where only the cortex of the mandible is cut, leaving all bone marrow, nerve and blood vessels intact, at two points on opposite sides of the mandible. The device is an expandable distraction device attached to the teeth of the mandible on opposite sides of the two points of the corticotomy surgery, and the expandable distraction device is then periodically expanded until a desired mandibular length is attained.

The method further comprises preparing the expandable distraction device for attachment during the corticotomy surgery. This includes fitting a plurality of stainless steel crowns onto the teeth of the mandible, taking an impression of the teeth of the mandible, removing the crowns from the teeth of the mandible and placing the crowns in the impression, preparing a solid model of the teeth of the mandible from the impression, the crowns being located on the solid model, and then attaching the expansion screw devices to the crowns.

Preferably, two expansion screw devices and two sliding tube devices are attached to eight crowns fitted onto the teeth of the mandible in the step of fitting, including two bicuspid and two molar crowns on each side of the mandible.

The impression is preferably a rubber base impression that is poured up with dental stone or plaster. The expansion screw devices and sliding tube devices are soldered to the crowns by means of sliding (removable) attachments according to the present invention in a very precise three dimensional location.

The expandable distraction device is subsequently expanded in the desired direction of the distraction of the mandible. The screw devices separate the crowns on each side of the mandible from each other at the point of the corticotomy surgery on the mandible. Preferably, the expandable screw devices are expanded at a rate of 1 mm per day, starting the day of the surgery.

The objects of the present invention are thus met by the provision of attachments for a mandibular distraction device having first and second sets of tooth crowns (or possibly bands), a first set of expandable screw and tube devices connected to the first set of tooth crowns and a second set of expandable screw and tube devices connected to the second set of tooth crowns.

The attachments for use with the mandibular distraction device comprise a receptor attachment adapted to be connected with a tooth engagement member of a mandibular distraction device, the receptor comprising a first metal member having a tooth engagement member connection portion and a connector receiving portion, and a connector attachment adapted to be connected with an expander assembly of a mandibular distraction device, the connector attachment comprising a first metal member comprising an expander assembly connection portion and a receptor connection portion that is engageable with the connector receiving portion of the receptor attachment.

The connector receiving portion of the receptor attachment may comprise a connector guide extending thereon, and the receptor connection portion of the connector comprises an engagement surface complementary to the connector guide of the receptor for removable engagement therewith.

The first metal member may comprise a back portion defining the tooth engagement member connection portion and a front portion defining the connector guide. The connector guide comprises a vertical slot open at front and upper areas thereof and closed at a back area and a lower area thereof. The lower area defines a vertical stop, and the slot tapers from the back area adjacent to the back portion toward the front area. The second metal member may comprise a plug having a front portion defining the expander assembly connection portion and a plug portion that extends vertically and has a taper complementary to the vertical slot of the first metal member.

The first metal member may also comprise a back portion defining the tooth engagement member connection portion and a front portion defining the connector guide. The connector guide comprises a vertically tapering front member having a pair of vertically extending flanges thereon, defining spaces between the front portion and the tooth engagement member connection portion, and a vertical stop. The second metal member may alternately comprise a cap having a front portion defining the expander assembly connection portion and a rear surface engageable with the front portion of the first metal member and channel members on the front portion of the second metal member that extend vertically and have a taper complementary to the vertically tapering front member of the connector guide. The front portion of the second metal member is engageable with the vertical stop.

The vertically extending flanges may have secondary flanges extending therefrom toward the toward the back portion of the first metal member, thus forming glue pockets that are adapted to receive glue for gluing the cap to the receptor. The first metal member may have a vertical alignment hole therein extending from an upper surface thereof. The cap can also have a slot extending horizontally across the front portion thereof at the lower end thereof. The back portion of the first metal member can also comprise horizontally extending tabs so as to be fixable to two tooth engagement members.

The first and second metal members of the receptor attachment and the connector attachment are preferably made of stainless steel and solderable to tooth engagement members.

Through the employment of mandibular distraction osteogenesis according to the present invention, using the attachments for the mandibular distraction device according to the present invention, a number of significant advantages may be achieved. As noted above, the procedure will orthodontically lengthen the mandible while minimizing the extent of the conjunctive lower jaw surgery. Only corticotomy is employed.

Further, the procedure will improve the facial profile by advancing or lengthening the deficient mandible. This will improve the lip balance, lip competence, and lip seal. This will also help to eliminate mouth breathing pattern problems. Further, incisor guidance and function will be established.

The procedure will also reduce the orthodontic-surgical treatment time. Treatment time can be expected to be reduced to on the order of 12 months, instead of 30 months as with the prior art sagittal split osteotomy surgery.

The procedure will also bring the mandible forward, thus bringing the tongue forward and diminishing chances for obstructive sleep apnea or snoring. Such correction will also help to prevent class II mandibular deficiency/malocclusion. The invention will help to correct unilateral cross bites and the mandibular midline.

Further, the procedure will minimize damage to the periosteal and endosteal blood supply by performing a corticotomy only, rather than a complete osteotomy as is now performed with the sagittal split osteotomy surgery. This will minimize swelling and post-surgical complications, and requires no hospital stay and could be done on an outpatient basis. Furthermore, the fact that the expansion screw assemblies are detachable from the receptor assemblies means that the orthodontist will generally not need to be present during surgery. The precise pre-alignment will have been done during fitting in the office.

Further, the procedure will be far less expensive than the conventional mandibular osteotomy surgery. Patient costs for the procedure are lower than the costs associated with prior art methods such as the sagittal split osteotomy surgery. Obviously this will tend to lower health care costs in general, which is a great concern at this time.

Other significant advantages result to the benefit of the patient. The procedure according to the present invention results in less pain to the patient than the prior art procedure. The recovery period after completion of the procedure is on the order of two to three days, rather than two months as with other methods. The jaw of the patient does not have to be wired shut for two months, and the patient is able to return to work within one week, as opposed to eight weeks with other methods. Thus it is clear that the psychological impact of the procedure on the patient will be significantly reduced as compared with the impact of the prior art methods.

BRIEF DESCRIPTION OF THE DRAWINGS

The present invention will be described in detail below with reference to the accompanying drawings, in which.

DETAILED DESCRIPTION OF THE PREFERRED EMBODIMENTS OF THE INVENTION

A detailed description of the present invention will now be presented with reference to the accompanying drawing figures. In the various figures, the same reference numerals are used for similar elements throughout. The description of the invention will proceed with the description of a mandibular distraction osteogenesis device and in particular Razdolsky attachments that are employed with the device for the purpose of securing expansion screws and sliding tubes onto the stainless steel crowns in a precise angular fashion and making both expansion screws and sliding tubes removable prior to corticotomy surgery.

Figure 2:
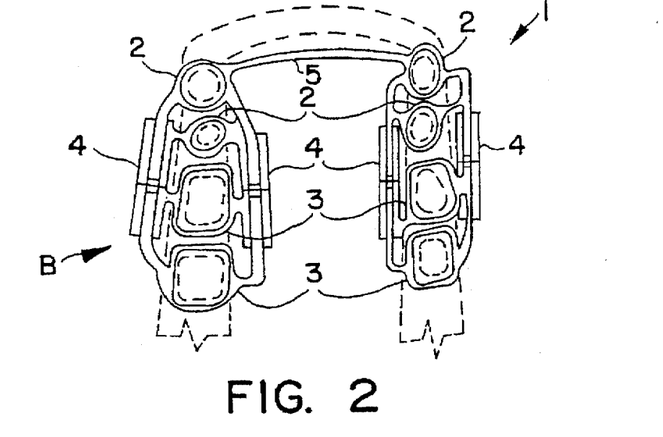
FIG. 2 is a top view of a mandibular distraction osteogenesis device according to the present invention.
Figure 3:
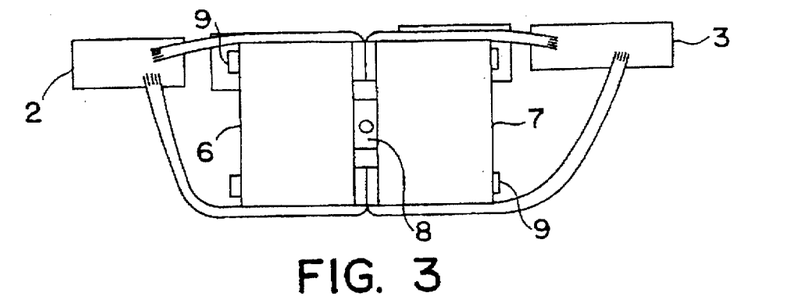
FIG. 3 is a side view of a portion of the mandibular distraction device as seen in the direction of arrow B of FIG. 2.

Turning to FIG. 2, there is illustrated a mandibular distraction osteogenesis device 1 usable in distracting the mandible. Initially, the device 1 includes a plurality of crowns (or bands, collectively also referenced as tooth engagement members) for placement on the teeth of the mandible of a patient that is to undergo distraction osteogenesis. The tooth engagement members of the present invention are preferably crowns, but it should be recognized that bands could also be employed instead of crowns; the description will primarily discuss crowns. In FIGS. 2 and 3, while the description references crowns, the illustration in these figures is not meant to be indicative of any particular type of crown but to be simply a generic description of a crown or band for purposes of illustration.

Preferably there are provided a total of eight crowns, with two bicuspid and two molar orthodontic crowns being provided for each side of the mandible, as illustrated in FIG. 2. The crowns are indicated by reference numbers 2 for the bicuspid crowns and reference numbers 3 for the molar crowns. The mandible and the relevant teeth are schematically illustrated by a dashed line in FIG. 2.

One universal expansion screw 4 is soldered onto each buccal (cheek) side of the crowns and one universal sliding tube device 5 is soldered onto each lingual (tongue) side of the crowns for each side of the mandible. One universal expansion screw 4 and one sliding tube 5 is thus placed on each side of each set of crowns. As can be seen from FIG. 2, the universal expansion screws thus extend along the sides of the crowns and have suitable portions thereof soldered to the respective crowns. The universal expansion screws 4 are expandable to distract a forward portion of the mandible, the upper portion as seen in FIG. 2, from a rearward portion of the mandible by separating the bicuspid bands 2 from the molar bands 3.

More specifically, and referring to FIG. 3, each universal expansion screw 4 has two halves 6 and 7 separable from each other by a screw mechanism 8. The screw mechanism 8 is a suitable mechanism rotatable between the universal expansion screw halves 6 and 7 to separate the halves from each other, such as a right and left hand threaded shaft extending into and engaging with corresponding threads in the halves 6 and 7. Suitable guide rods 9 can also extend through the halves 6 and 7 to guide the separation of the halves 6 and 7 from each other. As can be seen, suitable connecting portions are provided for connecting the halves 6 and 7 to the respective bands 2 and 3. Such connecting portions can take the form of appropriate metal wires or bars. The universal expansion screw 4 can be of the type illustrated in U.S. Pat. No. 4,482,318, for example, or could be of the type shown in U.S. Pat. No. 4,571,177, suitably adapted to the present situation. These patents are incorporated herein by reference.

By the above construction there is formed two separate portions of the mandibular distraction device 1, one portion being located on each side of the mandible. These portions are preferably connected to each other by a suitable connecting wire or bar 15, as illustrated in FIG. 2. However, note that in place of the connecting wire or bar 15, an additional, smaller, universal expansion screw 4 could be provided and incorporated into the device 1, the universal expansion screw connecting the two sides of the device 1 at the forward portions thereof in order to allow for lateral mandibular expansion, in addition to mandibular distraction or elongation.

As can be seen from FIG. 2, the bicuspid crowns 2 on each side of the mandible are connected to the forward portions or halves 6 of the universal expansion screws 4, and the molar crowns 3 are connected to the rear portions or halves 7 of the universal expansion screws 4. Thus, a unitary forward portion is expansible in a forward direction relative to two separate lateral portions on opposite sides of the mandible for elongation or distraction of the mandible.

Though not specifically illustrated, the sliding tubes 5 represent simple expandable sliding tube and pin connections connecting the forward and rearward portions of the device 1 on each side of the mandible. These tube and pin connections have a simple tube receiving a pin with the tube connected to one portion and the pin connected to the other portion and extending in the same direction as the expansion screws 4. Thus these devices will simply follow the distraction of the mandible along with the activation of the screw devices 4, but will provide for support on the lingual side of the crowns in all directions except for the direction of expansion. Such sliding tubes, as well as the expansion screws and crowns, are separately readily available from orthodontic suppliers.

While the above described distraction device 1 simply solders the expansion screws and sliding tubes 5 to the crowns 2 and 3, it is preferred that specific attachments be employed for this purpose, as will be described below. These attachments, generally referred to as Razdolsky attachments, comprise receptor attachments for attachment to the respective crowns, preferably by soldering, and connector attachments for connection to the respective screw devices and sliding tubes 5 also by soldering. The receptors and connectors are thus removably engageable with each other so that the screw devices 4 and sliding tubes 5 can be removably attached to the crowns, for reasons as will be discussed below in describing the method of mandibular distraction osteogenesis in accordance with the device of the present invention. At this point, specific description of the Razdolsky attachments will be made.

Figure 5:
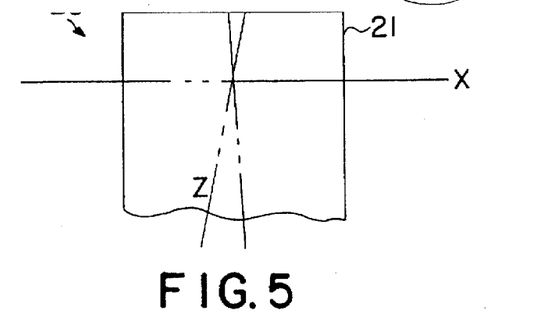
FIG. 5 is a partial perspective view of a Razdolsky attachment plug according to a first embodiment of attachments for the mandibular distraction device according to the present invention.
Figure 6:
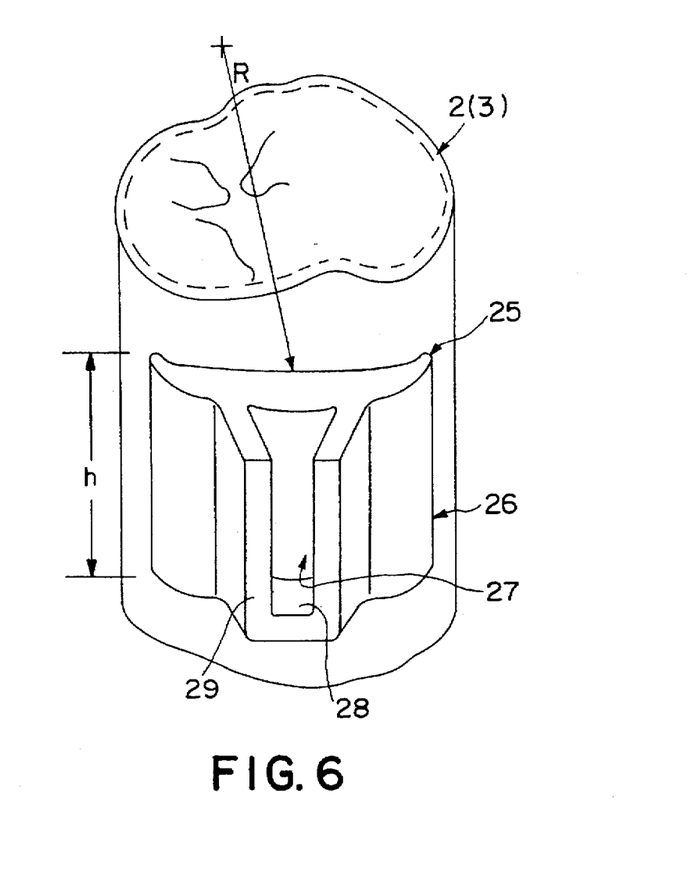
FIG. 6 is a perspective view of a receptor according to the first embodiment of the Razdolsky attachments, the receptor being mounted on a crown.
Figure 7:
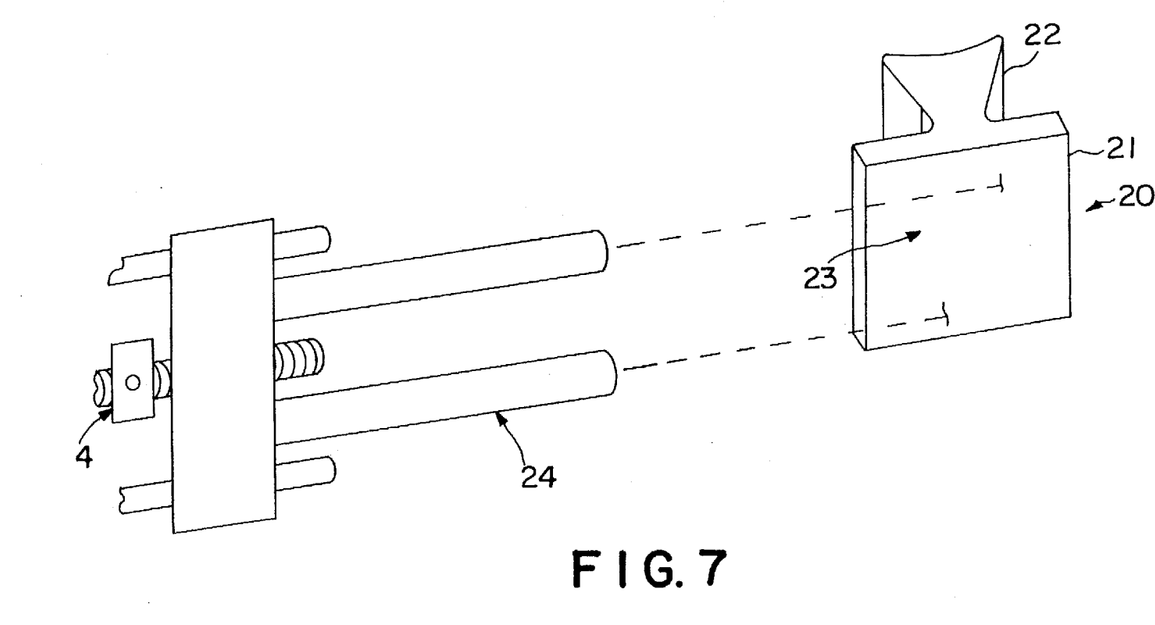
FIG. 7 is an exploded view of the plug and a screw device according to the first embodiment of the Razdolsky attachments.

A first embodiment of the Razdolsky attachments is illustrated in FIGS. 5–7. FIG. 5 illustrates a plug attachment for attachment to a screw device 4, FIG. 6 illustrates a crown 2 or 3 having a connector 25 connected therewith and FIG. 7 illustrates a connection between the screw device 4 and the plug 20.

The attachment plug 20 according to the Razdolsky attachments comprises a front portion 21 having a front surface and a plug portion 22. The plug portion 22 tapers from its distal end in the Z direction to the front portion 21, as illustrated.

FIG. 6 illustrates a stainless steel crown 2 or 3, preferably a stainless deep drawn thin shell molar or bicuspid cap as are commercially available. The receptor 25 is soldered to the stainless steel cap, and is preferably itself an investment cast stainless steel, etc. Solder flow details are provided on each side as illustrated at 26, noting the beads on the vertical sides of the receptor 25. The majority of the receptor 25 comprises the back portion soldered to the cap. A slot 27 is formed by a front portion 29, which has outwardly jutting walls defining the slot 27 as a slot tapering from the back portion toward the front. The slot is opened at its top and forward sides, and is closed at the back and lower portions thereof. The lower portion at 28 forms a vertical stop.

As seen in FIG. 7, expansion device solder legs 24 of the screw device 4 can be soldered to the front portion 21 of the plug 20 as noted at 23, designating a solder surface on the plug 20. During assembly, the plug 20 can then have its plug portion 22 vertically inserted into the slot 27 of the receptor 25, the plug 22 being complementary to the slot 27 for a snug fit. The plug 22 can be a solder plug and can provide a snug fit with a very low viscosity adhesive joint in the receptor 25.

The receptor 25 has a height h and a radius of its back surface R. The receptor 25 can thus be provided in several general ranges of sizes for general ranges of the sizes of teeth.

Figure 8:
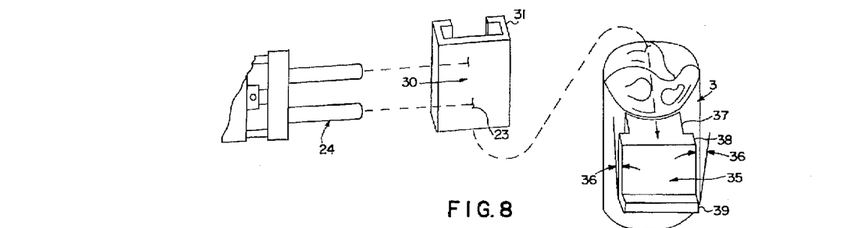
FIG. 8 is an exploded view of a screw device, a cap and a receptor according to a second embodiment of the Razdolsky attachments according to the present invention.

A second embodiment of the Razdolsky attachments is illustrated by FIG. 8. In this figure, the attachments comprise a cover or cap 30 in place of the plug, and a receptor 35. The receptor 35 is illustrated as attached to a molar crown 3, for example by soldering. The receptor 35 has a front portion 38 having lateral flanges with respect to the back portion 37 that is connected to the crown 3. The flanges have a slight taper shown at 36. The cap or cover 30 has flanges or channel members 31 forming channels for engagement with the flanges of the front portion 38. When engaged as illustrated, the slight taper wedges the cap or cover 30 in place, and the cap 30 engages a vertical stop 39 on the bottom of the receptor 35.

Figure 9:
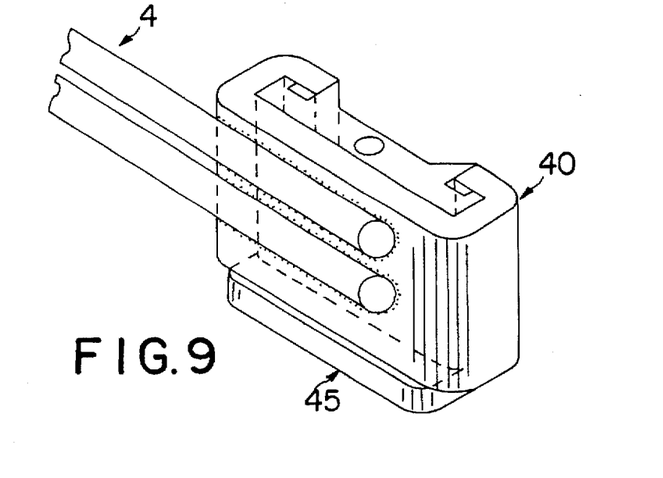
FIG. 9 is a perspective view of a cap and a receptor according to a third embodiment of the Razdolsky attachments of the present invention.
Figure 10:
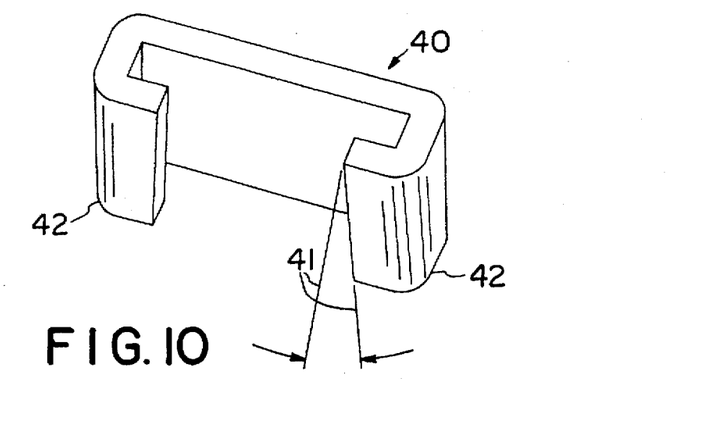
FIG. 10 is a perspective view of the cap of FIG. 9.
Figure 11:
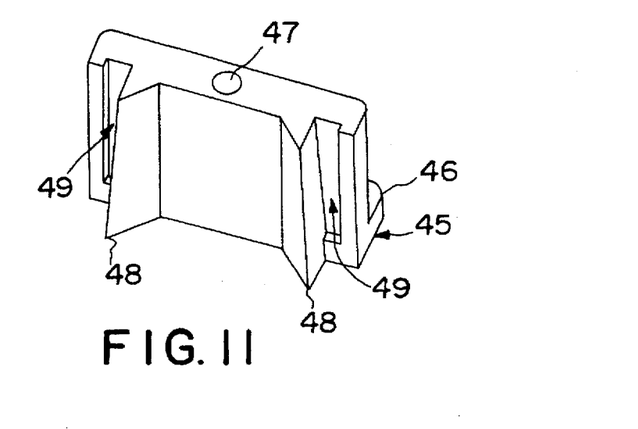
FIG. 11 is a perspective view from the rear of the receptor of FIG. 9.

FIGS. 9–11 illustrate a third embodiment according to the Razdolsky attachments of the present invention. In this embodiment, the cap 40 engages a receptor 45. The receptor 45 has a vertical stop 46 similar to the above embodiments, and an alignment hole 47. The cap 40 has channels 42 for engaging the rear surface of the receptor 45, with the turned flanges of the channels 42 having a taper at 41. The taper is provided for a tight fit against triangular engagement members 48 on the receptor 45, which are similarly tapered. According to a particular feature of this embodiment, glue pockets 49 are provided on the back surface of the receptor 45 for gluing the cap 40 to the receptor 45 during surgery.

Figure 12:
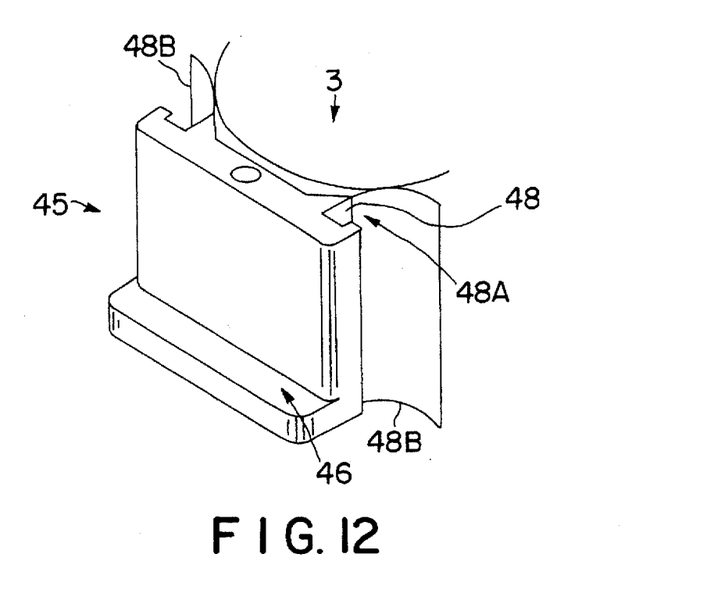
FIG. 12 is a perspective view of a receptor according to a modification of the third embodiment of the Razdolsky attachments.

In a variation of the third embodiment illustrated in FIG. 12, bendable wings 48b can be soldered at 48a to the rear engagement portions 48 of the receptor 45. These bendable wings can engage a molar cap 3.

Figure 13:
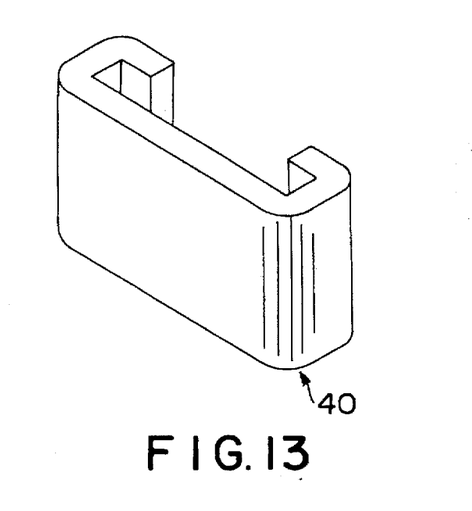
FIG. 13 is a perspective view of a cap suitable for use with the receptor of FIG. 12.

FIG. 13 provides a front perspective view of the cap 40 according to the third embodiment of the Razdolsky attachments of the present invention.

Figure 14:
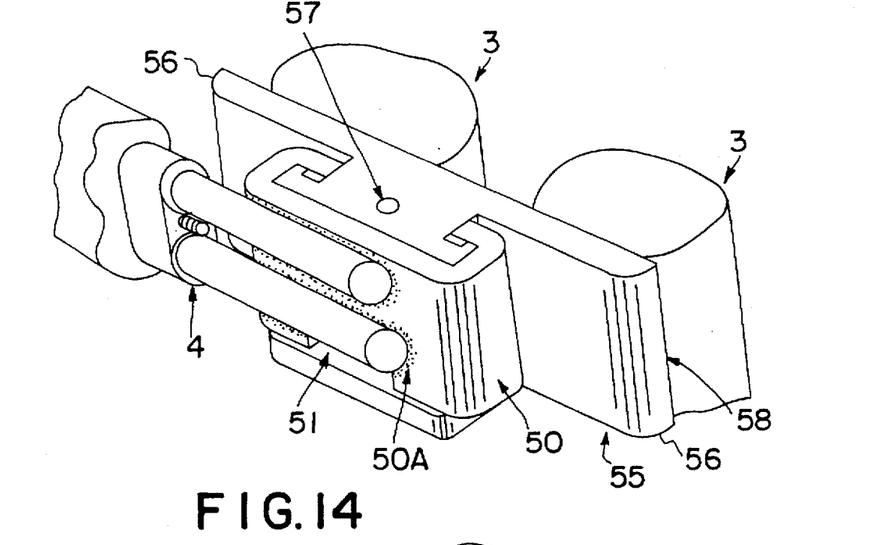
FIG. 14 is a perspective view of a screw device, cap and receptor according to a fourth embodiment of the Razdolsky attachments of the present invention.
Figure 15:
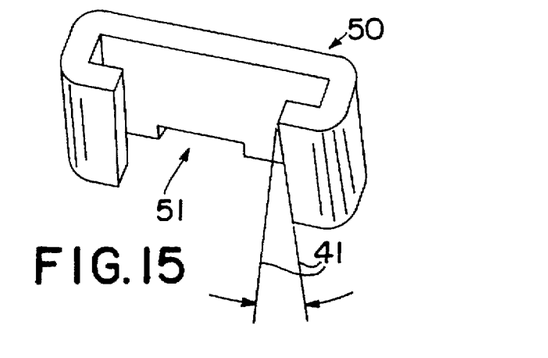
FIG. 15 is a perspective view of the cap of FIG. 14.
Figure 16:
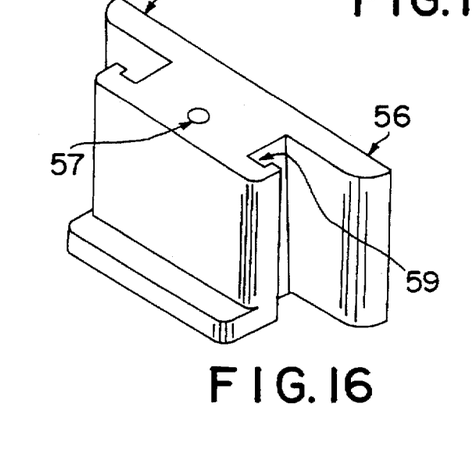
FIG. 16 is a perspective view of the receptor of FIG. 14.

FIGS. 14–16 describe a fourth embodiment of the Razdolsky attachments according to the present invention. A cap 50 is similar to the cap discussed with respect to the third embodiment of the Razdolsky attachments and is connected to the screw device 4 in a similar manner. However, in this embodiment a slot 51 is provided in the cap for receipt of a pry bar for removal of the cap from the receptor during an intermediate step of the procedure. It will be recognized that the slot could be provided with the other embodiments of the connectors of the present invention. A receptor 55 of this embodiment is similar to the receptor of the third embodiment of the Razdolsky attachments in that it has a similar front portion providing a vertical stop and an alignment hole 57, and provides similar glue pockets at the rear surface of the front portion. However, with this embodiment the rear portion is extended further back and connected with two laterally extending tabs 56 so that the single receptor 55 may be connected with two molar caps 3 as illustrated in FIG. 14. As seen at 58, the tabs 56 are soldered to the stainless steel caps. Thus employment of this embodiment will reduce the number of receptors and caps necessary for connection of the expansion screw devices 4 and sliding tube devices 5 on the sides of the lines of crowns. This will be further discussed below.

Figures 17, 18A, 18B:
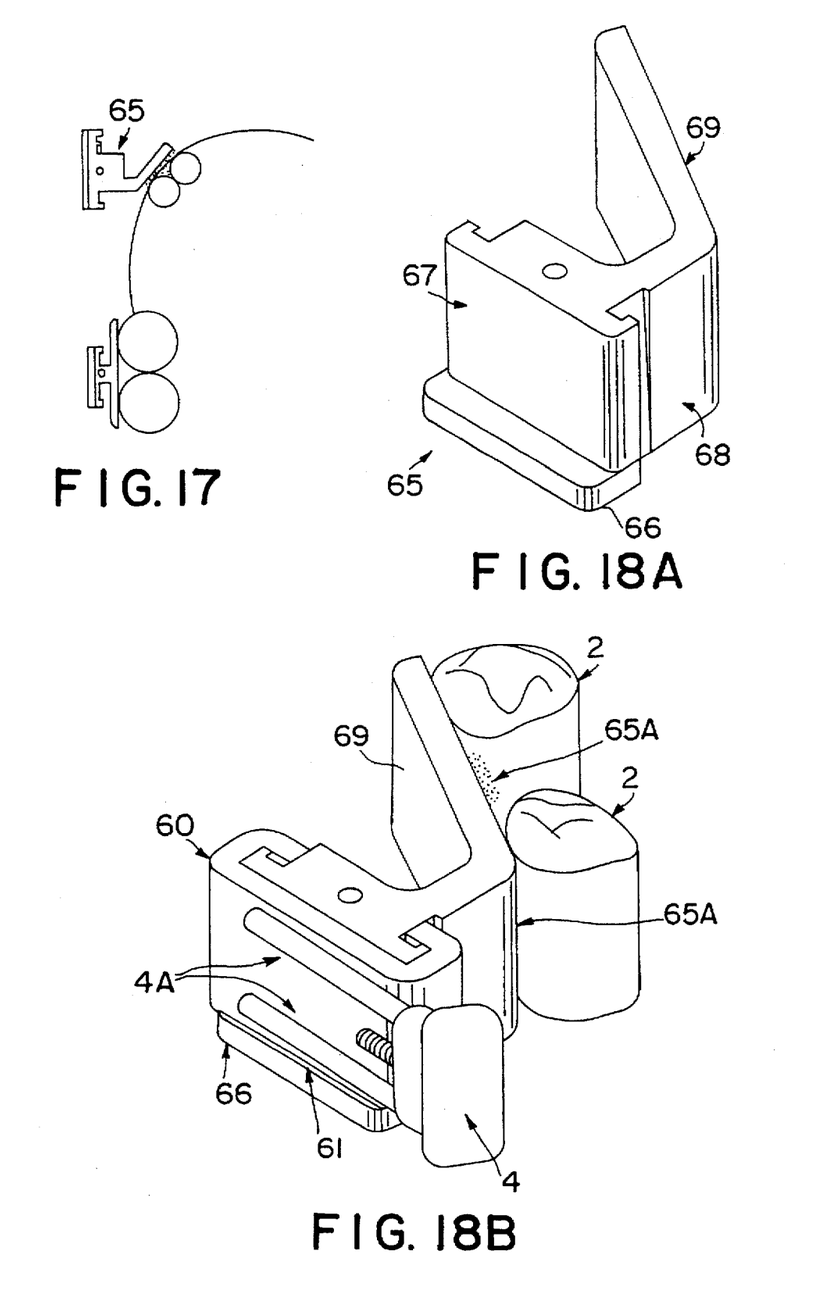
FIG. 17 is a schematic view of a receptor according to the fourth embodiment of the Razdolsky attachments used together with the receptor according to a fifth embodiment of the Razdolsky attachments of the present invention.
FIG. 18A is a perspective view of the receptor according to the fifth embodiment of the Razdolsky attachments.
FIG. 18B is a perspective view of a screw device, cap and receptor according to the fifth embodiment.

FIGS. 17–18B illustrate a fifth embodiment of the Razdolsky attachments according to the present invention, and can be used together with the fourth embodiment. That is, in this embodiment a receptor 65 has a front portion 67 with a vertical stop 66 similar to that of the third and fourth embodiments. However, instead of having the laterally extending tabs of the fourth embodiment, an intermediate portion 68 extends rearwardly from one side of the rear surface of the front portion 67, and continues into a back portion 69 that extends from the intermediate portion 68 at an angle that is acute relative to the direction of the expander assemblies. The cover 60 is similar to the previous embodiments and is provided with a pry slot 61 for engagement by a suitable tool, such as a thin bladed screwdriver, etc. As illustrated in FIG. 18B, the back portion 69 is soldered at 65a to two bicuspid crowns 2. The angle of the portion 69 allows the front 67 to be better aligned with respect to the assembly of the screw device 4 with its respective caps soldered thereto. In this regard, note FIG. 17. In this figure, two bicuspid caps are seen as connected with the receptor 65 and two molar caps are seen as connected with the receptor 55 according to the fourth embodiment. As seen in the figure, by the angled rear portion 69 of the receptor 65, both the front portions of the respective receptors can be aligned with reach other, making the process of assembly a simple matter.

With respect to the fifth embodiment, the bicuspid receptor 65 that is illustrated in FIG. 18A is obviously only usable on one side of the distraction device, i.e. on one side of the mandible. However, it is contemplated that a symmetric bicuspid receptor could be manufactured that would be usable on both sides of the mandible so that only one part would have to be manufactured.

Figure 4:
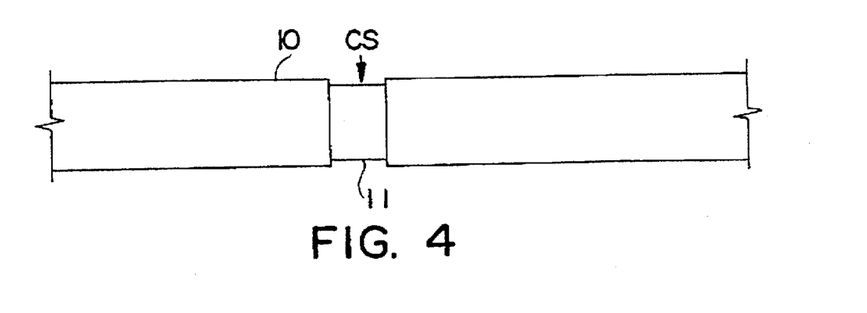
FIG. 4 is a schematic representation of corticotomy surgery.

The method of mandibular distraction osteogenesis using the Razdolsky attachments according to the present invention is as follows. Referring to FIGS. 2–4, first two bicuspid and two molar orthodontic crowns are fitted onto the respective teeth of a patient's mandible on each side of the mandible. Thus, a total of eight crowns are fitted onto the teeth of the patient. A rubber base impression is then taken of the patient's mandible with the crowns in place. The crowns are then removed and placed into the impression. Then, the impression is poured up with orthodontic (dental) stone or plaster, so as to form a model of the patient's mandible, with the crowns in place thereon on the appropriate teeth of the mandible model.

Figure 19A:
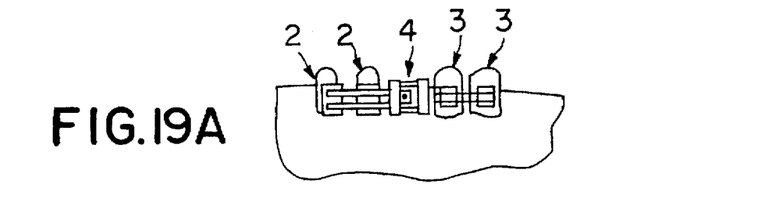
FIGS. 19A–19D are illustrations of steps in the process of using the present invention.

The two universal expansion screws 4 are then soldered onto the connectors of the Razdolsky attachments and the receptors are soldered onto the crowns (FIG. 19A) in a very precise angular fashion preferably using the laboratory instrument discussed in U.S. patent application Ser. No. 08/222,579 (incorporated herein by reference), filed Apr. 4, 1994. Two sliding tubes are also soldered onto the crowns 2 and 3 in a simple fashion utilizing the Razdolsky attachments. Thus the mandibular distraction device 1 is formed. A suitable connection 15 (FIG. 2, which shows the embodiment not using the attachments) may also be provided, or an additional universal expansion screw 4 may also be provided in place thereof to provide for lateral mandibular expansion. With the finished mandibular distraction device 1, the device is now ready to be cemented into the patient's mouth.

Figure 19B:
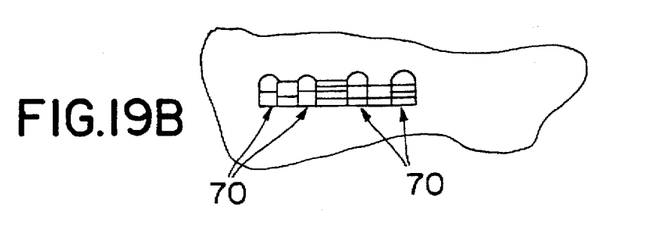
Figure 19C:
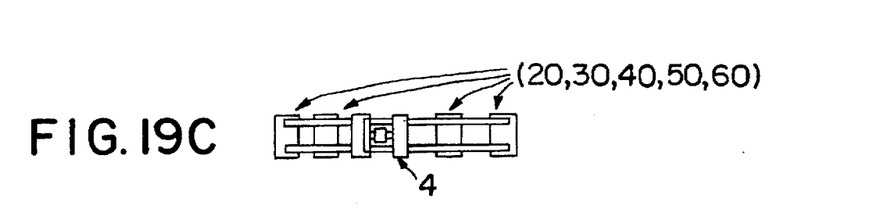
Figure 19D:
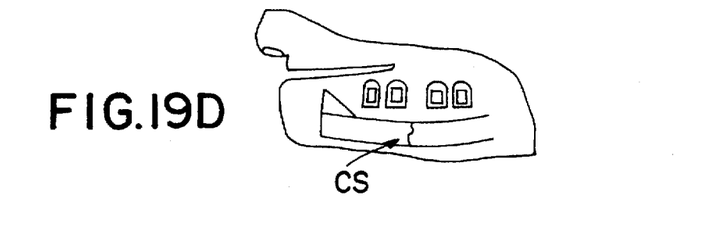

Accordingly, the mandibular distraction device is cemented into the patient's mouth prior to corticotomy surgery as at 70 (FIG. 19B). All expansion screws and sliding tubes are then removed (FIG. 19C) by means of the Razdolsky attachments, which guarantee the previous exact angular positioning, and are only to be reinserted after the corticotomy surgery is performed. When the screw devices and sliding tubes are removed by the use of the Razdolsky attachments, the crowns stay cemented on the patient's teeth. This technique provides for maximum access and visibility during the surgery. Corticotomy surgery is then performed, which is the cutting of the outside layer (cortex) only of the mandible (FIG. 19D). Referring to FIG. 4, a section of the patient's mandible is schematically illustrated. Portion 10 represents the outer layer of the bone, i.e. the cortex. This portion is cut during the corticotomy surgery. However the bone marrow 11 is left intact. This reduces the chance of the nerves or the blood vessels being severed. The location of the corticotomy surgery is represented in FIG. 4 by the letters CS. The corticotomy surgery is performed at two points on opposite sides of the mandible to allow for the elongation or distraction of the forward portion of the mandible from the rearward portion thereof. The corticotomy preferably takes place posterior to the lower second bicuspids, and preferably between the bicuspids and the molars on each side of the mandible to allow for the two bicuspid crowns 2 on each side to be displaced forwardly from the rear molar crowns 3 with the expansion of the universal expansion screws 4. Appropriate x-rays can be taken of the mandible in order to determine the exact thickness of the cortex to ensure that the bone marrow 11 is not cut.

After the reinsertion of the expansion screws and sliding tubes after corticotomy surgery, the mandible is then distracted by expanding the two universal expansion screws 4 inside of the patient's mouth. This is accomplished by rotating the screws 8 of the universal expansion screws 4 periodically to extend the forward portion of the mandible from the rearward portion thereof. This is possible because the cortex has been cut in the corticotomy surgery. The bone marrow is softer tissue and allows for elongation to take place. Both bone and soft tissue regeneration will occur during the process of expanding the universal expansion screws 4 and distracting the mandible. Preferably, the mandible is distracted at a rate of 1 mm per day until the proper mandibular length is obtained. There may be differential expansion between the left and right sides in order to maintain expansion along the centerline of the mandible.

Note that when reinserting the expansion screws and sliding tubes, the respective connectors are connected with the respective receptors. At this time, the receptors and connectors are preferably permanently bonded to each other prior to adjustment of the mandible by a suitable adhesive. However, as an alternative to adhesive, it is contemplated that a locking mechanism could be provided between each connector and receptor. Such a locking mechanism would preferably be of a type in which the receptor and connector are securely fixed with each other, but which could be quickly released by the orthodontist or surgeon, and different types of such locking mechanisms will occur to those of skill in the art.

While preferred embodiments of the present invention have been described above in some particularity, the scope of the present invention should not be limited thereby, as various modifications thereof will be apparent to those of skill in the art.

We claim:

1. Attachments for use with a mandibular distraction device, comprising:
   a receptor attachment adapted to be connected with a tooth engagement member of a mandibular distraction device, said receptor attachment comprising a first metal member having a tooth engagement member connection portion and a connector receiving portion; and
   a connector attachment adapted to be connected with an expander assembly of a mandibular distraction device, said connector attachment comprising a second metal member comprising an expander assembly connection portion and a receptor connection portion that is engageable with said connector receiving portion of said receptor attachment;
   wherein said connector receiving portion of said receptor attachment comprises a connector guide extending thereon;
   wherein said receptor connection portion of said connector attachment comprises an engagement surface complementary to said connector guide of said receptor attachment for removable engagement therewith;

wherein said first metal member has a vertical stop thereon that projects outwardly of said connector guide so as to be able to stop said receptor connection portion of said connector attachment; and wherein said expander assembly connection portion comprises a planar surface facing away from said receptor attachment when said receptor connection portion is engaged with said connector receiving portion.

2. The attachments of claim 1, wherein:

said first metal member comprises a back portion defining said tooth engagement member connection portion and a front portion defining said connector guide, said connector guide comprising a vertically tapering front member having a pair of vertically extending flanges thereon, defining spaces between said front portion and said tooth engagement member connection portion, and a vertical stop; and said second metal member comprising a cap having a front portion defining said expander assembly connection portion and a rear surface engageable with said front portion of said first metal member and channel members on said front portion of said second metal member that extend vertically and have a taper complementary to said vertically tapering front member of said connector guide, said front portion of said second metal member being engageable with said vertical stop.

3. The attachments of claim 1, wherein said cap has a slot extending horizontally across said front portion thereof at a lower end of said cap.

4. The attachments of claim 1, wherein said back portion of said first metal member comprises horizontally extending tabs defining a means for connecting said first metal member to two tooth engagement members.

5. The attachments of claim 1, wherein first and second metal members of said receptor attachment and said connector attachment are made of stainless steel and are solderable to tooth engagement members.

6. Attachments for use with a mandibular distraction device, comprising:

a receptor attachment adapted to be connected with a tooth engagement member of a mandibular distraction device, said receptor attachment comprising a first metal member having a tooth engagement member connection portion and a connector receiving portion; and a connector attachment adapted to be connected with an expander assembly of a mandibular distraction device, said connector attachment comprising a second metal member comprising an expander assembly connection portion and a receptor connection portion that is engageable with said connector receiving portion of said receptor attachment;

wherein said connector receiving portion of said receptor attachment comprises a connector guide extending thereon;

wherein said receptor connection portion of said connector attachment comprises an engagement surface complementary to said connector guide of said receptor attachment for removable engagement therewith;

wherein said first metal member comprises a back portion defining said tooth engagement member connection portion and a front portion defining said connector guide, said connector guide comprising a vertically tapering front member having a pair of vertically extending flanges thereon, defining spaces between said front portion and said tooth engagement member connection portion, and a vertical stop;

wherein said second metal member comprises a cap having a front portion defining said expander assembly connection portion and a rear surface engageable with said front portion of said first metal member and channel members on said front portion of said second metal member that extend vertically and have a taper complementary to said vertically tapering front member of said connector guide, said front portion of said second metal member being engageable with said vertical stop; and wherein said vertically extending flanges have secondary flanges extending therefrom toward said back portion of said first metal member forming pockets.

7. Attachments for use with a mandibular distraction device, comprising:

a receptor attachment adapted to be connected with a tooth engagement member of a mandibular distraction device, said receptor attachment comprising a first metal member having a tooth engagement member connection portion and a connector receiving portion; and a connector attachment adapted to be connected with an expander assembly of a mandibular distraction device, said connector attachment comprising a second metal member comprising an expander assembly connection portion and a receptor connection portion that is engageable with said connector receiving portion of said receptor attachment;

wherein said connector receiving portion of said receptor attachment comprises a connector guide extending thereon;

wherein said receptor connection portion of said connector attachment comprises an engagement surface complementary to said connector guide of said receptor attachment for removable engagement therewith;

wherein said first metal member comprises a back portion defining said tooth engagement member connection portion and a front portion defining said connector guide, said connector guide comprising a vertically tapering front member having a pair of vertically extending flanges thereon, defining spaces between said front portion and said tooth engagement member connection portion, and a vertical stop;

wherein said second metal member comprises a cap having a front portion defining said expander assembly connection portion and a rear surface engageable with said front portion of said first metal member and channel members on said front portion of said second metal member that extend vertically and have a taper complementary to said vertically tapering front member of said connector guide, said front portion of said second metal member being engageable with said vertical stop; and wherein said front portion of said first metal member has a vertical alignment hole extending therein from an upper surface thereof.

8. Attachments for use with a mandibular distraction device, comprising:

a receptor attachment adapted to be connected with a tooth engagement member of a mandibular distraction device, said receptor attachment comprising a first metal member having a tooth engagement member connection portion and a connector receiving portion; and a connector attachment adapted to be connected with an expander assembly of a mandibular distraction device, said connector attachment comprising a second metal member comprising an expander assembly connection portion and a receptor connection portion that is engageable with said connector receiving portion of said receptor attachment;

wherein said connector receiving portion of said receptor attachment comprises a connector guide extending thereon;

wherein said receptor connection portion of said connector attachment comprises an engagement surface complementary to said connector guide of said receptor attachment for removable engagement therewith;

wherein said first metal member comprises a back portion defining said tooth engagement member connection portion and a front portion defining said connector guide, said connector guide comprising a vertically tapering front member having a pair of vertically extending flanges thereon, defining spaces between said front portion and said tooth engagement member connection portion, and a vertical stop;

wherein said second metal member comprises a cap having a front portion defining said expander assembly connection portion and a rear surface engageable with said front portion of said first metal member and channel members on said front portion of said second metal member that extend vertically and have a taper complementary to said vertically tapering front member of said connector guide, said front portion of said second metal member being engageable with said vertical stop;

wherein said first metal member of said receptor attachment comprises a front portion defining said connector guide, said connector guide comprising a pair of vertically extending flanges, a vertical stop on said front portion, an intermediate portion extending from said front portion and a back portion extending from said intermediate portion defining a means for connecting to at least one tooth engagement member, said intermediate portion spacing said back portion from said front portion; and wherein said second metal member of said connector comprises a cap having a front portion defining a means for connecting to an expander assembly, a rear surface engageable with said front portion of said first metal member and channel members on said front portion for engagement with said flanges, said front portion being engageable with said vertical stop.

9. Attachments for use with a mandibular distraction device, comprising:

a receptor attachment adapted to be connected with a tooth engagement member of a mandibular distraction device, said receptor attachment comprising a first metal member having a tooth engagement member connection portion and a connector receiving portion; and a connector attachment adapted to be connected with an expander assembly of a mandibular distraction device, said connector attachment comprising a second metal member comprising an expander assembly connection portion and a receptor connection portion that is engageable with said connector receiving portion of said receptor attachment;

wherein said connector receiving portion of said receptor attachment comprises a connector guide extending thereon;

wherein said receptor connection attachment portion of said connector comprises an engagement surface complementary to said connector guide of said receptor attachment for removable engagement therewith;

wherein said first metal member comprises a back portion defining said tooth engagement member connection portion and a front portion defining said connector guide, said connector guide comprising a vertical slot open at front and upper areas thereof and closed at a back area and a lower area thereof, said lower area defining a vertical stop, and said slot tapering from said back area adjacent to said back portion toward said front area;

wherein said second metal member comprises a plug having a front portion defining said expander assembly connection portion and a plug portion that extends vertically and has a taper complementary to said vertical slot of said first metal member; and wherein said expander assembly connection portion comprises a planar surface facing away from said receptor attachment when said receptor connection portion is engaged with said connector receiving portion, said planar surface extending horizontally in a direction perpendicular to said vertical slot a greater distance than the horizontal width of said vertical slot.

10. Attachments for use with a mandibular distraction device, comprising:

a receptor attachment adapted to be connected with a tooth engagement member of a mandibular distraction device, said receptor attachment comprising a first metal member having a tooth engagement member connection portion and a connector receiving portion; and a connector attachment adapted to be connected with an expander assembly of a mandibular distraction device, said connector attachment comprising a second metal member comprising an expander assembly connection portion and a receptor connection portion that is engageable with said connector receiving portion of said receptor attachment;

wherein said connector receiving portion of said receptor attachment comprises a connector guide extending thereon;

wherein said receptor connection portion of said connector attachment comprises an engagement surface complementary to said connector guide of said receptor attachment for removable engagement therewith; and wherein said first metal member has a vertical alignment hole extending therein.

* * * * *